US00PP35704P3

(12) United States Plant Patent
MacGregor et al.

(10) Patent No.: US PP35,704 P3
(45) Date of Patent: Mar. 26, 2024

(54) ***GERANIUM* PLANT NAMED 'MACGER002'**

(50) Latin Name: ***Geranium maculatum* L.**
Varietal Denomination: MACGER002

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 0 days.

(21) Appl. No.: 18/445,344

(22) Filed: Jul. 21, 2023

(65) Prior Publication Data

US 2024/0032447 P1 Jan. 25, 2024

(30) Foreign Application Priority Data

Jul. 21, 2022 (QZ) ..... PBR 2022/1754

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./263.1, 324
See application file for complete search history.

*Primary Examiner* — Karen M Redden
(74) *Attorney, Agent, or Firm* — Samuel R. McCoy, Jr.

(57) ABSTRACT

'MACGER002' is a new and distinctive variety of *Geranium maculatum* plant which is characterized by long-lasting, dark brown foliage and dark pink flowers with small white floral eye. The new variety propagates successfully by stem cuttings and tissue culture and has shown to be uniform and stable in the resulting generations from asexual propagation.

3 Drawing Sheets

Latin name of the genus and species: The Latin name of the genus and species of the novel variety disclosed herein is *Geranium maculatum* L.

Variety denomination: The inventive variety of *Geranium* disclosed herein has been given the variety denomination 'MACGER002'.

CROSS REFERENCE TO RELATED APPLICATIONS

This application claims priority to the Community Plant Variety Rights application number 2022/1754, filed Jul. 21, 2022, which is herein incorporated by reference.

BACKGROUND OF THE INVENTION

Parentage: 'MACGER002' is the result of a controlled cross-pollination breeding program carried out by the inventors at their commercial nursery in Kirkcudbright, Scotland, in the summer of 2015. The inventors performed a controlled cross-pollination of the emasculated seed parent, an unnamed *Geranium maculatum* plant developed by the inventors (unpatented) with *Geranium maculatum* 'Spring Purple' (unpatented), the pollen parent. Said pollination was performed in an insect proof environment. Seed from the cross was harvested, then germinated, and the resulting seedlings were then grown to a mature size in a protected poly tunnel greenhouse. In May of 2016, the inventors selected the new *Geranium* cultivar for its vivid flower color and dark foliage. This new and distinctive cultivar was given the name 'MACGER002'.

Asexual Reproduction: Asexual reproduction of 'MACGER002' was first accomplished in 2016 by way of vegetative division in Kirkcudbright, Scotland, and subsequently by way of meristematic tissue culture micro propagation at a laboratory in Heerhugowaard, the Netherlands. Four successive generations have shown that the unique features of the instant cultivar are stable and reproduce true to type.

SUMMARY OF THE INVENTION

The cultivar 'MACGER002' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Geranium* cultivar, 'MACGER002'.

1. *Geranium* 'MACGER002' exhibits an abundance of long-lasting dark brown foliage; and
2. *Geranium* 'MACGER002' exhibits foliage that is deeply cleft; and
3. *Geranium* 'MACGER002' exhibits violet-purple flowers, generally appearing dark pink, with a small white floral eye.

BOTANICAL DESCRIPTION OF THE PLANT

Figure 1:
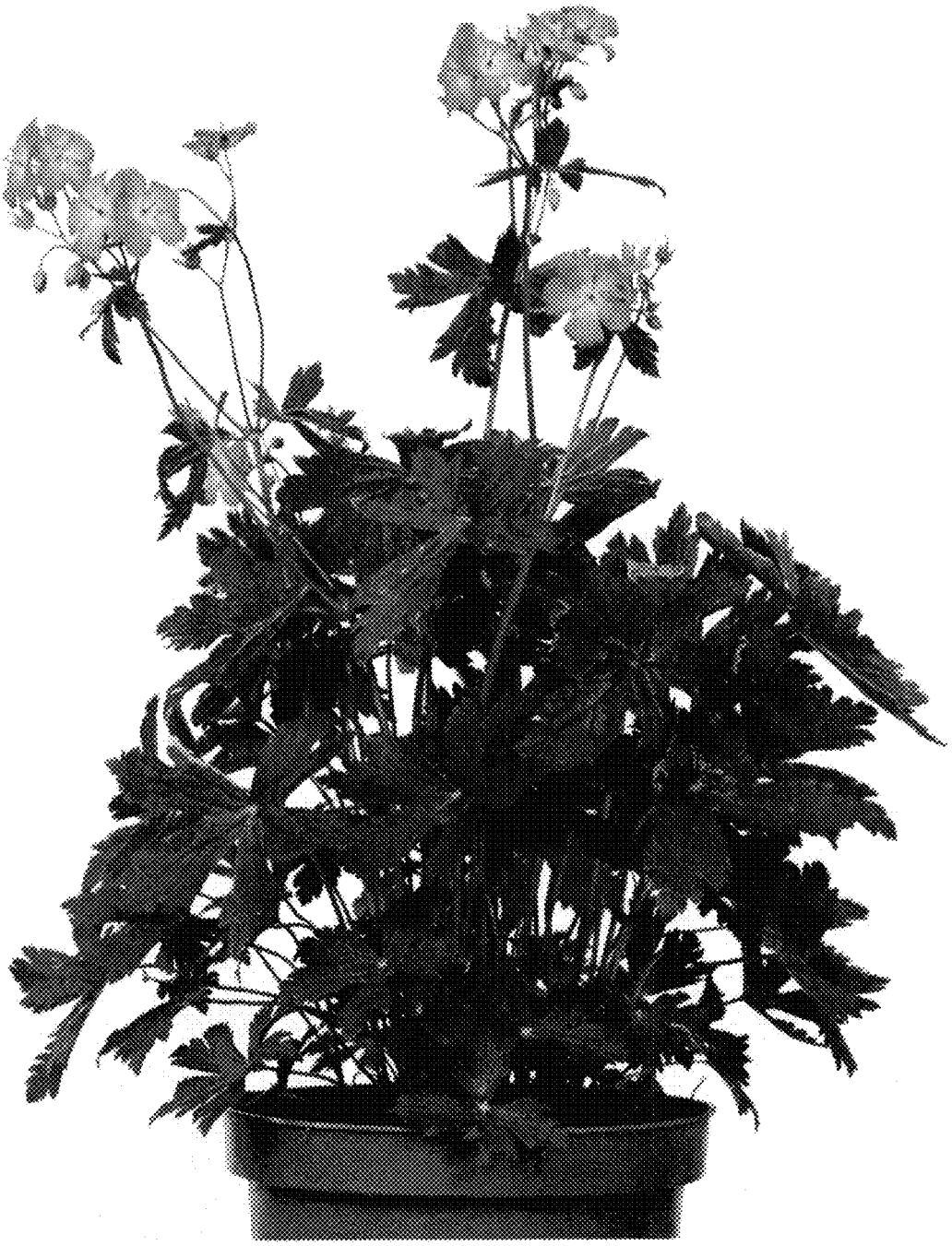
FIG. 1 shows, as nearly true as it is reasonably possible to make the same in color illustrations of this type, an exemplary plant of 'MACGER002' grown in a commercial greenhouse in Kirkcudbright, Scotland. This plant is approximately 1-year-old, shown planted in a 17 cm container.
Figure 2:
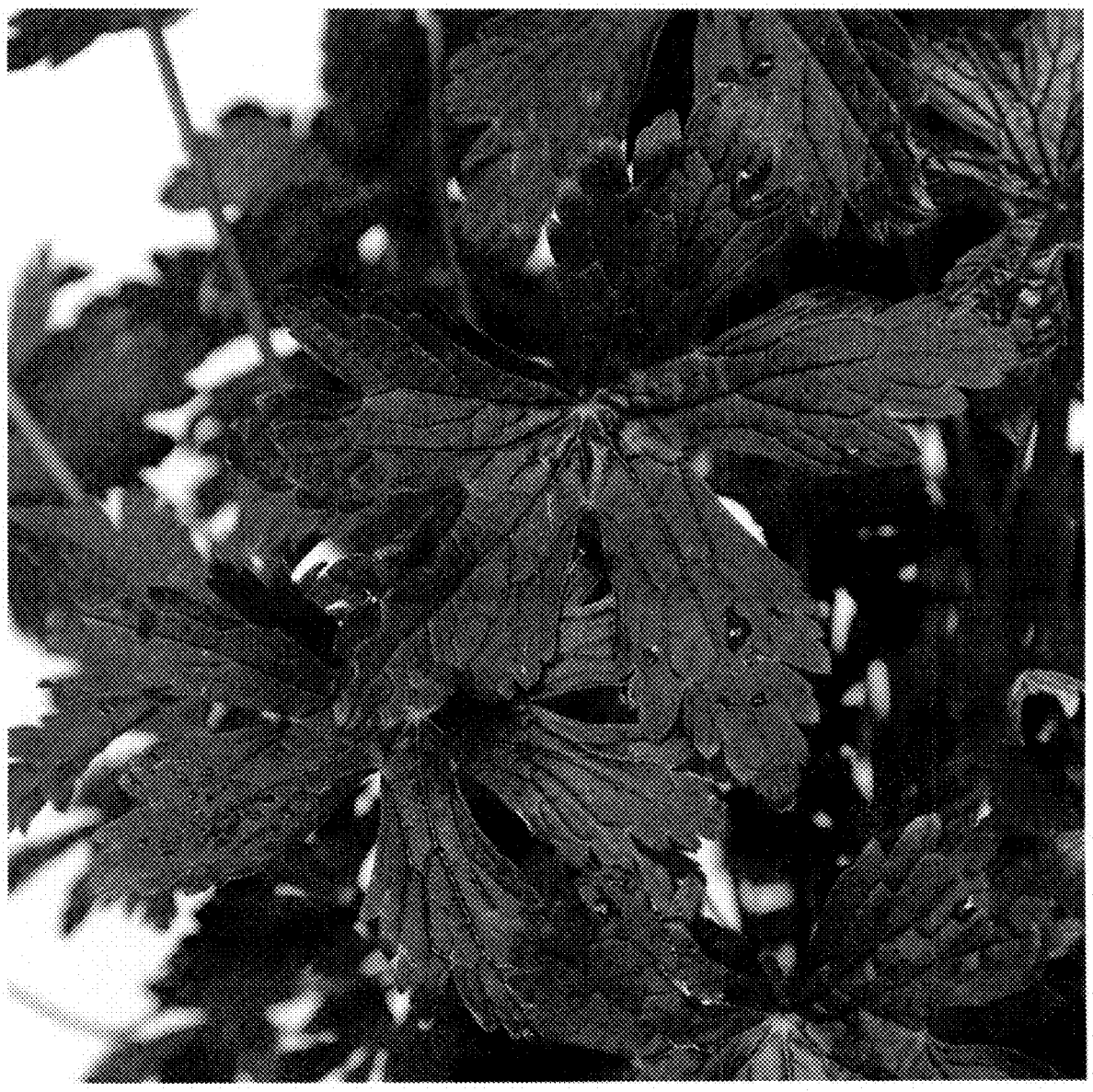
FIG. 2 shows, as nearly true as it is reasonably possible to make the same in color illustrations of this type; the typical mature foliage of 'MACGER002'.
Figure 3:
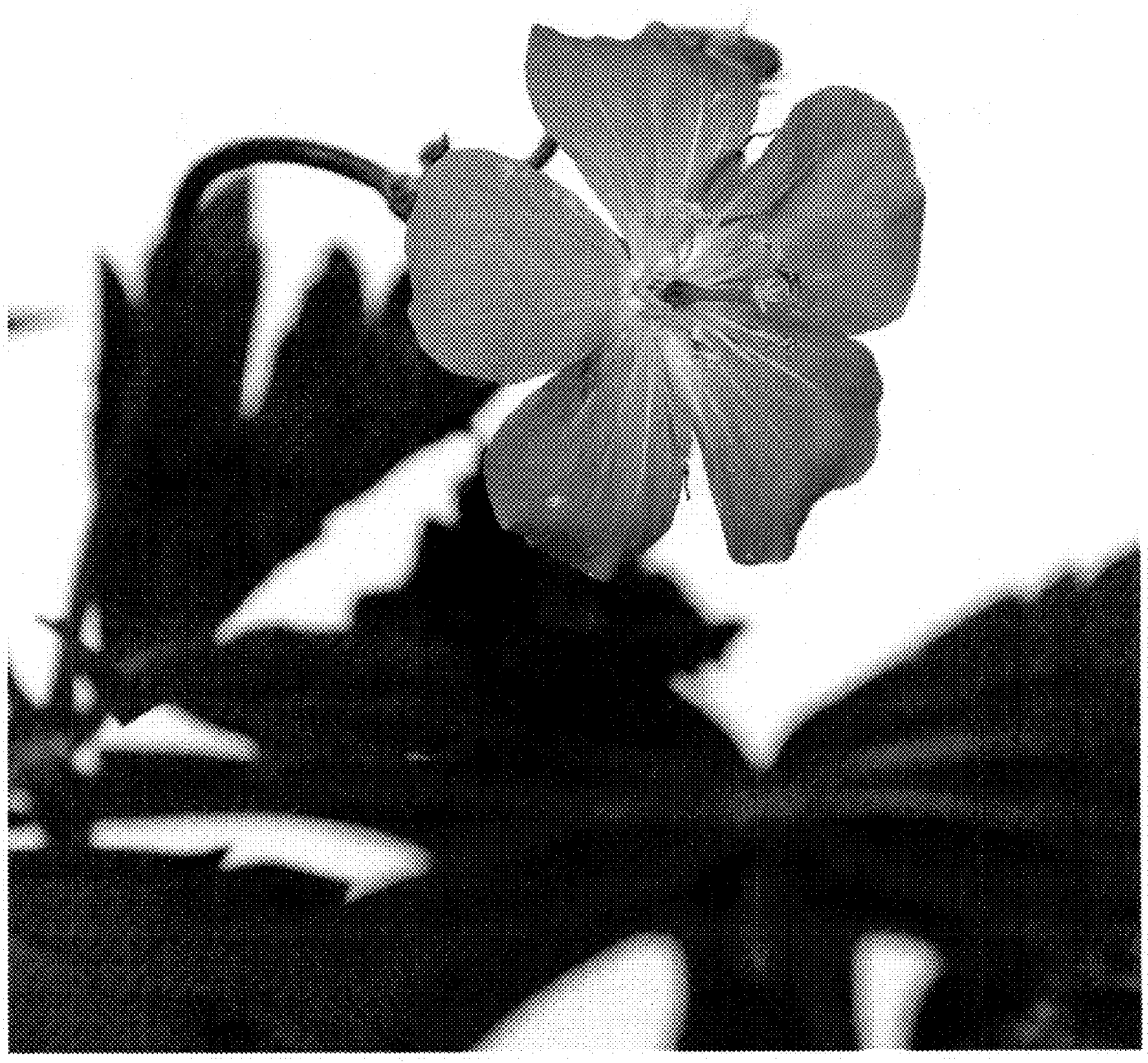
FIG. 3 shows, as nearly true as it is reasonably possible to make the same in color illustrations of this type, the typical flower of 'MACGER002'.

The following is a detailed botanical description of a new and distinct variety of *Geranium* plant known as 'MACGER002', based upon observations of 12-month-old plants grown in 17 cm nursery containers in Kirkcudbright, Scotland. Plants were grown in a vented, unheated greenhouse with partial shade exposure. Plants were manually watered as needed and fertilized with a slow-release granular fertilizer which was incorporated into the growing media. No chemical pest treatments were given to the plants. Observation data was recorded in May of 2022.

A botanical description of 'MACGER002' and comparisons with the parents and most similar variety of common knowledge are provided below.

General plant description:

*Growth habit.*—Broad-spreading herbaceous perennial with flowering stems arising from the base, and inflorescence held above the foliar plane.

*Plant profile.*—Globular.

*Height.*—34.5 cm to the top of the foliar plane; 42.3 cm to the top of the floral plane.

*Spread.*—44.0 cm..

*Plant vigor.*—Very vigorous.

*Growth rate.*—Fast growing.

*Propagation.*—Method — Meristematic tissue culture. Time to initiate rooting — Approximately 10 to 14 days at an average ambient temperature of 22 degrees Celsius. Time to produce flowering plant from rooted cutting — Approximately 4 months in a 15 cm container.

*Pest resistance and susceptibility.*—Plants have not been observed to be any more or less susceptible or resistant to pathogens and pests known to affect *Geranium* sp.

*Environmental tolerances.*—Adapt to, at least, USDA Zones 5 to 9 and temperatures ranging from minus 23 degrees Celsius to 35 degrees Celsius; moderate tolerance to rain; moderate tolerance to wind.

Root system:

*Description.*—A moderately dense network slightly fleshy, non-fibrous lateral roots.

*Rooting habit.*—Moderately branched and evenly distributed throughout the soil profile.

*Root diameter.*—2.0 mm at the base, on average.

*Texture.*—Smooth; glabrous.

*Color.*—Greyed-orange, nearest to RHS 165B.

Stem:

*Branching habit.*—Basally and laterally branched; moderately free branching.

*Number of primary (main)stems per plant.*—6.

*Number of secondary (lateral) branches per plant.*—6.

*Attitude.*—Upright and slightly outward, at an average angle of 20 degrees from vertical.

*Aspect.*—Rounded.

*Length.*—33.1 cm.

*Diameter.*—0.3 cm.

*Internode length.*—16.4 cm.

*Texture.*—Sparsely covered with short, glandular hairs; hairs are colored white, nearest to RHS N155A, and are 0.6 mm long, on average.

*Luster.*—Moderately glossy.

*Strength.*—Moderately strong.

*Color, juvenile.*—Greyed-purple, nearest to RHS 187C.

*Color, mature.*—Greyed-red, nearest to RHS 178A; stem surfaces that are shielded from ultraviolet light are greyed-orange, nearest to RHS 177B.

*Color at internodes.*—Greyed-orange, nearest to RHS 177B, and strongly suffused with greyed-purple, nearest to RHS 184B.

Foliage:

*Arrangement.*—Leaves are borne both basally and on stems; basal leaf arrangement is alternate and leaves on stems are arranged oppositely.

*Basal leaves.*—Attachment — Petiolate. Division — Simple. Quantity — An average of 6 leaves per stem. Leaf shape — Deeply palmate, with an average of five deeply cleft lobes, occasionally seven, and a reniform to near orbicular profile. Lobes — Depth of sinuses — Deep. Sinus orientation — Convergent. Dimensions — 10.2 cm long, excluding the petiole, and 11.7 cm wide. Leaf attitude — Outward, at an average angle of 80 degrees to the stem. Leaf apex — Acute. Leaf base — Hastate with basal lobes free. Leaf margin — Coarsely serrate. Texture, adaxial and abaxial surfaces — Slightly rugose; pubescent. Pubescence, adaxial surface — Sparsely to moderately covered with short hairs with an average length of 0.3 mm; colored greyed-white, nearest to RHS 156D. Pubescence, abaxial surface — Sparsely to moderately covered with short hairs, particularly along the veins, with an average length of 0.2 mm; colored greyed-white, nearest to RHS 156D. Luster, adaxial surface — Very slightly glossy. Luster, abaxial surface — Slightly glossy. Color — Juvenile foliage color, adaxial surface — Nearest to a mixture of greyed-brown and brown, RHS 166A and 200B yet closest to 200B. Juvenile foliage color, abaxial surface — Greyed-orange, nearest to RHS 166A. Mature leaf color, adaxial surface — Brown, nearest to RHS 200A, and fading lighter towards the apex, nearest to RHS 200B. Mature leaf color, abaxial surface — Nearest to a mixture of greyed-brown and brown, RHS N199B and 200C. Venation — Type — Palmate. Vein color, adaxial surface — Brown, nearest to RHS 200A. Vein color, abaxial surface — Yellow-green, nearest to RHS N148A. Petiole — Length — 18.9 cm. Diameter — 0.225 cm. Strength — Strong. Texture, adaxial and abaxial surfaces — Moderately covered with soft hairs; average length of hairs is 0.05 cm; colored white, nearest to RHS N155A. Luster, adaxial and abaxial surfaces — Slightly glossy. Color, adaxial surface — Greyed-brown, nearest to RHS 199B, and fading to greyed-purple, distally, nearest to RHS 187C. Color, abaxial surface — Yellow-green, nearest to RHS 152A, and suffused with greyed-purple, distally, nearest to RHS 183B. Stipules — General — Two leafy stipules present at the base of each leaf. Shape — Lanceolate. Length — 0.5 cm. Diameter — 0.15 cm. Apex — Acuminate. Base — Broad cuneate. Margins — Serrate. Texture, adaxial and abaxial surfaces — Slightly to moderately pubescent. Luster, adaxial and abaxial surfaces — Slightly glossy. Color, adaxial surface — Yellow-green, nearest to RHS 150D, and tipped brown, nearest to RHS 200B. Color, abaxial surface — Yellow-green, nearest to RHS 150D, and tipped brown, nearest to RHS 200B.

*Leaves borne on the stems.*—Quantity — Approximately 6 leaves per stem. Attachment — Petiolate. Division — Simple. Leaf shape — Deeply palmate, with an average of five deeply cleft lobes, occasionally seven, and a reniform to near orbicular profile. Lobes — Depth of sinuses — Deep. Sinus orientation — Convergent. Dimensions — 7.0 cm long, excluding the petiole, and 9.0 cm wide. Leaf attitude — Leaves in an average angle of 80 degrees to the stem. Leaf apex — Acute. Leaf base — Hastate with basal lobes free. Leaf margin — Coarsely serrate. Texture, adaxial and abaxial surfaces — Slightly rugose; pubescent. Pubescence, adaxial surface — Sparsely to moderately covered with short hairs with an average length of 0.3 mm; colored greyed-white, nearest to RHS 156D. Pubescence, abaxial surface — Sparsely to moderately covered with short hairs, particularly along the veins, with an average length of 0.2 mm; colored greyed-white, nearest to RHS 156D. Luster, adaxial surface — Very slightly glossy. Luster, abaxial surface — Slightly glossy. Color — Juvenile foliage color, adaxial surface — Nearest to a mixture of greyed-brown and brown, RHS 166A and 200B yet closest to 200B. Juvenile foliage color, abaxial surface — Greyed-orange, nearest to RHS 166A. Mature leaf color, adaxial surface — Brown, nearest to RHS 200A, and fading lighter towards the apex, nearest to RHS 200B. Mature leaf color, abaxial surface — Nearest to a mixture of greyed-brown and brown, RHS N199B and 200C. Venation — Type — Palmate. Vein color, adaxial surface — Brown, nearest to RHS 200A. Vein color, abaxial surface — Yellow-green, nearest to RHS N148A. Petiole — Length — 1.6 cm. Diameter — 0.15 cm. Strength — Strong. Texture, adaxial and abaxial surfaces — Moderately covered with soft hairs; average length of hairs is 0.05 cm; colored white, nearest to RHS N155A. Luster, adaxial and abaxial surfaces — Slightly glossy. Color, adaxial surface — Greyed-purple, nearest to RHS N187C, and fading lighter, proximally, nearest to RHS 187C. Color, abaxial surface — Greyed-purple, nearest to RHS 183C, and fading to greyed-orange, proximally, nearest to RHS 177B. Stipules — General — Two leafy stipules present at the base of each leaf. Shape — Lanceolate. Length — 0.5 cm. Diameter — 0.15 cm. Apex — Acuminate. Base — Broad cuneate. Margins — Serrate. Texture, adaxial and abaxial surfaces — Slightly to moderately pubescent. Luster, adaxial and abaxial surfaces — Slightly glossy. Color, adaxial surface — Yellow-green, nearest to RHS 150D, and tipped brown, nearest to RHS 200B. Color, abaxial surface — Yellow-green, nearest to RHS 150D, and tipped brown, nearest to RHS 200B.

Inflorescence:

*Habit.*—Dichotomous cyme with two pedicellate flowers borne at the end of the peduncle.

*Dimensions.*—10.1 cm long and 7.9 cm wide, at the widest point across the outstretched flowers of the cyme.

*Natural flowering season.*—Spring into summer in Kirkcudbright, Scotland.

*Time to flower or response time.*—Approximately 9 months.

*Quantity of open flowers per plant.*—14, on average.

*Quantity of flower buds per plant.*—58, on average.

*Quantity of flowers and flower buds per plant.*—72, on average.

*Peduncles.*—Length — Average of 10.7 cm. Diameter — Average of 1.75 cm. Angle — Average angle to stem is 30 degrees. Strength — Moderately strong. Texture — Lightly pubescent; hairs are soft with an average length of 0.8 mm; colored white, nearest to RHS N155A. Luster — Slightly glossy. Color — Greyed-purple, nearest to RHS 183B.

Flower buds:

*Shape.*—Ovate.

*Length.*—1.0 cm.

*Diameter.*—0.55 cm.

*Texture.*—Smooth and glabrous, with the exception of the margins; margins are sparsely covered with soft hairs with an average length of 0.6 mm; colored white, nearest to RHS N155A.

*Luster.*—Very slightly glossy.

*Color.*—Green, nearest to in between RHS 143B and 143C; axially striped with greyed-purple, nearest to RHS 187A; apex is violet-purple, nearest to RHS N80A.

Flower:

*Shape, type.*—Rotate; single.

*Flowering habit.*—Freely flowering.

*Aspect.*—Upright to outward.

*Flower longevity on plant.*—Approximately seven days.

*Persistent or self-cleaning.*—Self-cleaning.

*Fragrance.*—Non-fragrant.

*Diameter.*—3.4 cm.

*Depth.*—1.2 cm.

*Pedicels.*—Length — 1.0 cm. Diameter — 0.1 cm. Angle — Average angle to peduncle is approximately 30 degrees. Strength — Moderately strong. Texture — Smooth and densely pubescent; hairs are soft with an average length of 0.6 mm; colored white, nearest to RHS N155A. Luster — Moderately glossy. Color — Greyed-purple, nearest to RHS 183B.

*Calyx.*—Shape — Rotate. Length — 0.7 cm. Diameter — 1.8 cm. Sepals — Arrangement — Rotate. Quantity — 5 unfused sepals. Shape — Ovate. Aspect — Slightly concave. Dimensions — 1.1 cm long and 0.45 cm wide. Apex — Mucronate. Base — Cuneate. Margin — Entire; no undulation; sparsely covered with short, soft hairs with an average length of 0.6 mm and colored white, nearest to RHS N155A. Texture and luster, upper surface — Smooth, glabrous, and very slightly glossy. Texture and luster, lower surface — Smooth, glabrous, and very slightly glossy. Color — When opening, upper surface — Yellow-green, nearest to RHS 146B; margined green, RHS 143B; tipped greyed-orange, RHS 177A. When opening, lower surface — Yellow-green, nearest to RHS 144B; main vein is brown, RHS N200A; tipped greyed-orange, RHS 177A. Fully opened, upper surface — Yellow-green, nearest to RHS 146B; margined green, RHS 143B; tipped greyed-orange, RHS 177A; not fading. Fully opened, lower surface — Yellow-green, nearest to RHS 144B; main vein is brown, RHS N200A; tipped greyed-orange, RHS 177A; not fading. Venation — Fully opened, upper surface — Yellow-green, RHS 146B. Fully opened, lower surface — Brown, RHS N200A.

*Petals.*—Quantity — Five. Arrangement — Rotate; arranged in a single whorl of unfused petals. Length — 1.7 cm. Width — 1.4 cm. Shape — Broad obovate. Apex — Rounded. Base — Narrow cuneate. Margin — Entire; lightly undulated. Texture, upper surface — Glabrous, slightly velvety and matte; base is glossy. Texture, lower surface — Glabrous, very slightly velvety, and matte. Petal color — When opening, upper surface — Purple-violet, nearest to RHS N82A. Veins are purple-violet, nearest to RHS N80A, and fade to greyed-white towards the base, nearest to RHS 156C. When opening, lower surface — Purple-violet, nearest to RHS N82A. Veins are purple-violet, nearest to RHS N80A, and fade to greyed-white towards the base, nearest to RHS 156C. Fully opened, upper surface — Purple-violet, nearest to RHS N81B, and fading to greyed-white at the base, nearest to RHS 156C. Fully opened, lower surface — Purple-violet, nearest to RHS N81B, and fading to greyed-white at the base, nearest to RHS 156C. Venation, fully opened, upper surface — Green-white, nearest to RHS 156C. Venation, fully opened, lower surface — Green-white, nearest to RHS 156D. When faded, upper surface — Not fading. When faded, upper surface — Purple-violet, nearest to in between RHS N81B and N82C.

*Floral bracts.*—Position — Two bracts are present at the base of each pedicel. Shape — Lanceolate. Aspect — Flat. Length — 0.4 cm. Width — 0.1 cm. Apex — Acute Base — Broad cuneate. Margins — Entire. Color, adaxial and abaxial surfaces — Yellow-green, nearest to RHS 150D; tipped brown, nearest to RHS 200B. Texture, adaxial and abaxial surfaces — Glabrous.

Reproductive organs:

*Androecium.*—Stamens — Quantity — Approximately 10. Anthers — Shape — Oblong. Dimensions — 0.2 cm long and 0.1 cm wide. Color — Orange-white, nearest to RHS 159D. Filaments — Length — 0.7 cm. Color — Green-white, nearest to RHS 157D; fading to yellow-green towards the base, nearest to RHS 147D. Amount of Pollen — Sparse. Pollen color — Greyed-green, nearest to RHS 198B.

*Gynoecium.*—Pistil — Quantity — One. Length — 0.5 cm. Style — Length — 0.45 cm. Color — Greyed-orange, nearest to RHS 166D. Stigma — Quantity — Five. Shape — Curled. Length — 0.1 cm. Diameter — 0.4 cm. Color — Greyed-yellow, nearest to RHS 160D. Ovary Color — Brown, nearest to in between RHS N200A and N200B.

Seed and fruit:

*Fruit.*—Shape — Oblong. Quantity — 72. Dimensions — 2.5 cm long and 0.4 cm in diameter. Texture — Very sparsely covered with short hairs with an average length of 1.0 mm and colored white, nearest to RHS N155A. Color, mature fruit — Greyed-orange, nearest to RHS 174A, and fading to greyed-brown towards the base, nearest to in between RHS 199B and 199C. Persistent styles and stigmas are colored greyed-red, nearest to RHS 180B.

*Seed.*—No seeds have been detected.

Comparisons with the parent plants: Plants of the new cultivar 'MACGER002' differ from its seed parent, an unnamed *Geranium maculatum* plant (not patented), by the characteristics described in Table 1.

TABLE 1

| Characteristic | 'MACGER002' | The seed parent. |
|---|---|---|
| General coloration of the foliage. | Dark brown and not fading. | Light brown. |
| General coloration of the flower. | Violet-purple, generally appearing as dark pink. | Light pink. |

Plants of the new cultivar 'MACGER002' may be distinguished from its pollen parent, *Geranium maculatum* 'Spring Purple' (not patented), by the characteristics described in Table 2.

TABLE 2

| Characteristic | 'MACGER002' | 'Spring Purple' |
|---|---|---|
| General coloration of the foliage. | Dark brown and not fading. | Medium yellow-green foliage. |
| General coloration of the flower. | Violet-purple, generally appearing as dark pink. | Violet-purple, appearing more towards purple. |

Comparison with the most similar variety of common knowledge: Plants of the new cultivar 'MACGER002' may be distinguished from the most similar known commercial comparator, *Geranium maculatum* 'Espresso' (not patented), by the characteristics described in Table 3.

TABLE 3

| Characteristic | 'MACGER002' | 'Espresso' |
|---|---|---|
| General coloration of the mature foliage. | Dark brown and not fading. | Dark greyed-red to greyed-purple and fading to green suffused with greyed-red. |
| General coloration of the flower. | Violet-purple, generally appearing as dark pink. | Light pink. |

That which is claimed is:

1. A new and distinct variety of *Geranium maculatum* plant named 'MACGER002', substantially as described and illustrated herein.

* * * * *